United States Patent
Cai

(10) Patent No.: US 7,798,977 B2
(45) Date of Patent: Sep. 21, 2010

(54) DISPOSABLE BLOOD SAMPLING DEVICE

(75) Inventor: Jian Cai, Shanghai (CN)

(73) Assignee: Kun Shan Medsafe Medical Tech Co., Ltd., Jiangsu (CN)

( * ) Notice: Subject to any disclaimer, the term of this patent is extended or adjusted under 35 U.S.C. 154(b) by 599 days.

(21) Appl. No.: 11/781,237

(22) Filed: Jul. 21, 2007

(65) Prior Publication Data

US 2008/0097242 A1   Apr. 24, 2008

(30) Foreign Application Priority Data

Oct. 20, 2006   (TW) .............................. 95218599 U

(51) Int. Cl.
*A61B 5/00*   (2006.01)
*B65D 81/00*   (2006.01)

(52) U.S. Cl. .................. 600/577; 600/573; 600/575; 600/576; 600/578; 600/579

(58) Field of Classification Search ............... 600/300, 600/573, 575, 576, 577, 578, 579; 604/4.01, 604/6.12, 6.15, 6.16, 264, 265, 266, 269; 606/167, 184, 185; 73/864, 864.01, 864.11, 73/864.16, 864.81, 864.83, 864.85, 864.87
See application file for complete search history.

(56) References Cited

U.S. PATENT DOCUMENTS

| | | | | | |
|---|---|---|---|---|---|
| 3,734,079 | A | * | 5/1973 | Weber | 600/370 |
| 4,213,456 | A | * | 7/1980 | Bottger | 604/226 |
| 4,363,329 | A | * | 12/1982 | Raitto | 600/578 |
| 4,774,963 | A | * | 10/1988 | Ichikawa et al. | 600/576 |
| 4,840,185 | A | * | 6/1989 | Hernandez | 600/576 |
| 4,929,237 | A | * | 5/1990 | Medway | 604/198 |
| 4,932,945 | A | * | 6/1990 | Braginetz et al. | 604/195 |
| 4,969,454 | A | * | 11/1990 | Servello | 606/185 |
| 5,053,018 | A | * | 10/1991 | Talonn et al. | 604/198 |
| 5,112,327 | A | * | 5/1992 | Iinuma et al. | 604/413 |
| 5,195,985 | A | * | 3/1993 | Hall | 604/195 |
| 5,374,250 | A | * | 12/1994 | Dixon | 604/110 |
| 5,439,450 | A | * | 8/1995 | Haedt | 604/198 |
| 5,891,052 | A | * | 4/1999 | Simmons | 600/573 |
| 6,264,620 | B1 | * | 7/2001 | Shieh | 600/576 |
| 6,344,031 | B1 | * | 2/2002 | Novacek et al. | 604/195 |
| 6,488,666 | B1 | * | 12/2002 | Geist | 604/263 |
| 7,322,941 | B2 | * | 1/2008 | Henshaw | 600/578 |
| 7,351,228 | B2 | * | 4/2008 | Keane et al. | 604/218 |
| 2007/0060841 | A1 | * | 3/2007 | Henshaw | 600/578 |

* cited by examiner

*Primary Examiner*—Max Hindenburg
*Assistant Examiner*—Jeffrey G Hoekstra

(57) ABSTRACT

A disposable blood sampling device is disclosed herein, which includes a plunger, a rubber stopper, a barrel, a sealing member, a needle holder, a protection sleeve, an anticoagulant storing tube and a needle sheath. In use, the disposable blood sampling device is deconstructed by removing each component therefrom and is unable to be assembled again for recycling. Furthermore, the needle can be hidden in the protection sleeve before it is detached from the blood sampling device, which effectively prevents a medical operator from being hurt or even infected by the needle.

13 Claims, 25 Drawing Sheets

DISPOSABLE BLOOD SAMPLING DEVICE

BACKGROUND OF THE INVENTION

1. Field of the Invention

The present invention relates to a blood sampling device, in particular to a disposable blood sampling device.

2. The Prior Arts

A medical blood sampling device and an injector substantially have similar structures which include a barrel, a needle mounted on one end of the barrel and a plunger with a stopper inserted into the other end of the barrel and being axially movable in the barrel. By pushing or pull the plunger, blood or medical liquid can be drawn into or exhausted from the barrel. Particularly, the blood sampling device further requires another device for providing an anticoagulant to the barrel, such that the blood within the barrel can be prevented from coagulating.

Since the early blood sampling device is unsafe in use, it is often heard that a medical operator was hurt or even infected by the needle. Accordingly, a new blood sampling device with a protection device was proposed. However, such blood sampling device has to work with auxiliary accessories, which is inconvenient to use. Furthermore, the blood sampling device cannot be self-deconstructed after use, which leaves the worry that the used blood sampling device may be recycled. When this occurs, the medical operator or patient has higher risk of infection.

SUMMARY OF THE INVENTION

An objective of the present invention is to provide a disposable blood sampling device, which has greater safety in use. During the operation, the blood sampling device is deconstructed by removing each component therefrom and is unable to be assembled again for recycling. Furthermore, a needle can be hidden in a protection sleeve before it is detached from the blood sampling device, which effectively prevents a medical operator from being hurt by the needle and thus infected.

To achieve the above-mentioned objectives, a disposable blood sampling device comprises a plunger; a rubber stopper coupled to the one end of the plunger; a barrel having an axially extended tube body with a first end and a second end, wherein a chamber is defined in the tube body from the first end to the second end for inserting the plunger with the rubber stopper, and the second end has a needle connector communicated to the chamber, and a ring-shaped flange formed around a perimeter of the needle connector and having an inner spiral protrusion formed on an inner surface thereof; a sealing member, which is made of resilient material, having a first end and a second end opposite to the first end, wherein an outer spiral groove is formed on an outer circumferential surface of the sealing member for engaging with the inner spiral protrusion of the barrel, a blind hole is formed from the first end to the second end for receiving with the needle connector, a conical hole is formed on the second end, and a sealing hole is provided to connect the blind hole and conical hole and is sealed when there is no external force applied thereto and; a needle holder having a first end and a second end opposite to the first end, wherein a chamber is formed in the needle holder from the first end to the second end, the second end has a needle-holding hole communicated to the chamber, an outer circumferential surface of the needle holder has a plurality of guide notches, first longitudinal guide grooves connected to the guide notches, transversal guide grooves connected to the first longitudinal guide grooves, second longitudinal guide grooves connected to the transversal guide grooves, and an outer protrusion; a needle inserted into the needle-holding hole of the needle holder and the sealed hole of the sealing member; a protection sleeve having an axially extended tube body with a first end and a second end opposite to the first end, wherein a passage is confined by an inner wall of the tube body and is formed from the first end to the second end, the inner wall has a guide slot formed from the first end toward the second end, a longitudinal slot communicated to the guide slot for guiding the outer protrusion of needle holder and a step defined between the longitudinal slot and guide slot, an end of the longitudinal slot close to the first end of the protection sleeve has a through hole with an elastic member protruded to a center of the through hole, an inner circumferential surface of the protection sleeve close to the second end has an inner protrusion with an inner diameter smaller than an outer diameter of the outer protrusion of the needle holder; a needle sheath having an axially extended tube body with a first end and a second end opposite to the first end, wherein a chamber is formed in the needle sheath from the first end to the second end, and the first end has a lock slot fitted with an outer diameter of the needle holder; and an anticoagulant storing tube disposed in the chamber close to the second end of the needle sheath.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

Figure 1:
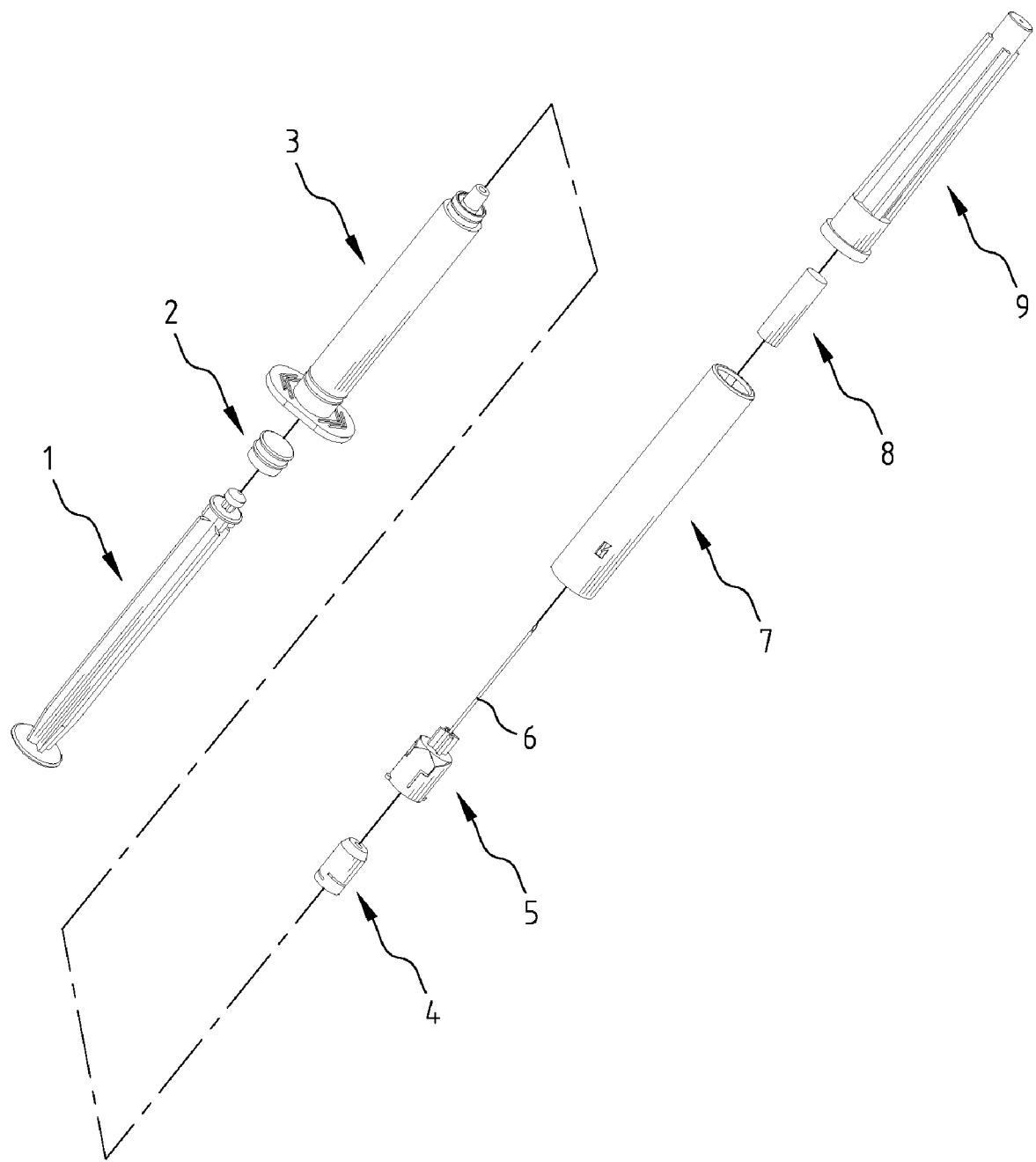
FIG. 1 is a perspective exploded view of a disposable blood sampling device according to the present invention.

Referring to FIG. 1, a disposable blood sampling device in accordance with the present invention comprises a plunger 1, a rubber stopper 2, an barrel 3, a sealing member 4, a needle holder 5, a needle 6, a protection sleeve 7, an anticoagulant storing tube 8 and a needle sheath 9.

Figure 2:
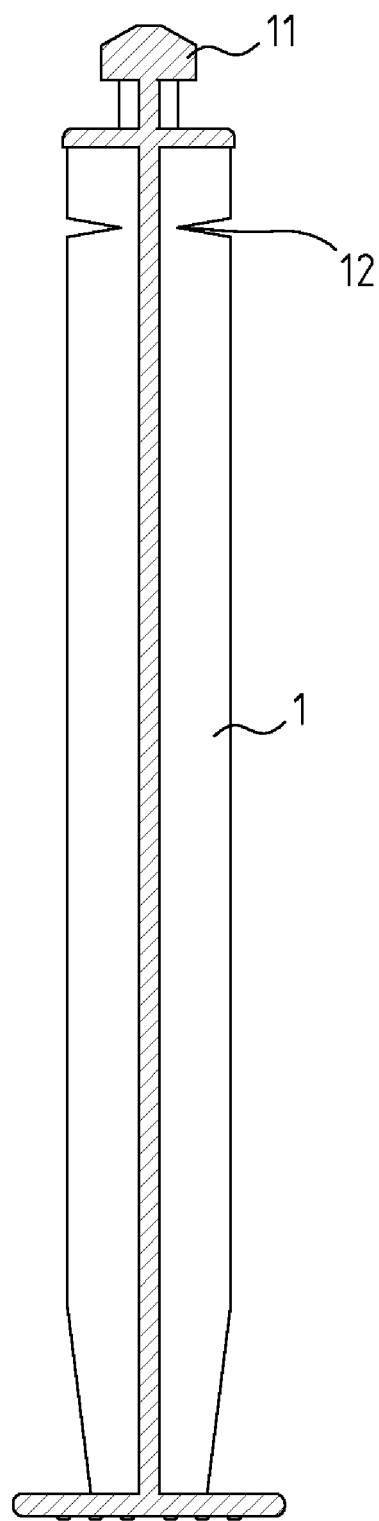
FIG. 2 is a cross sectional view of a plunger of the disposable blood sampling device according to the present invention.

As shown in FIG. 2, the plunger 1 has a first end and a second end located opposite to the first end. A fastening element 11 is disposed at the second end of the plunger 1 and a plurality of notches 12 extending from an outer perimeter to an axis of the plunger 1 close to the second end, such that the plunger 1 can be broken off for convenient disposal by applying a force to the notches 12.

Figure 3:
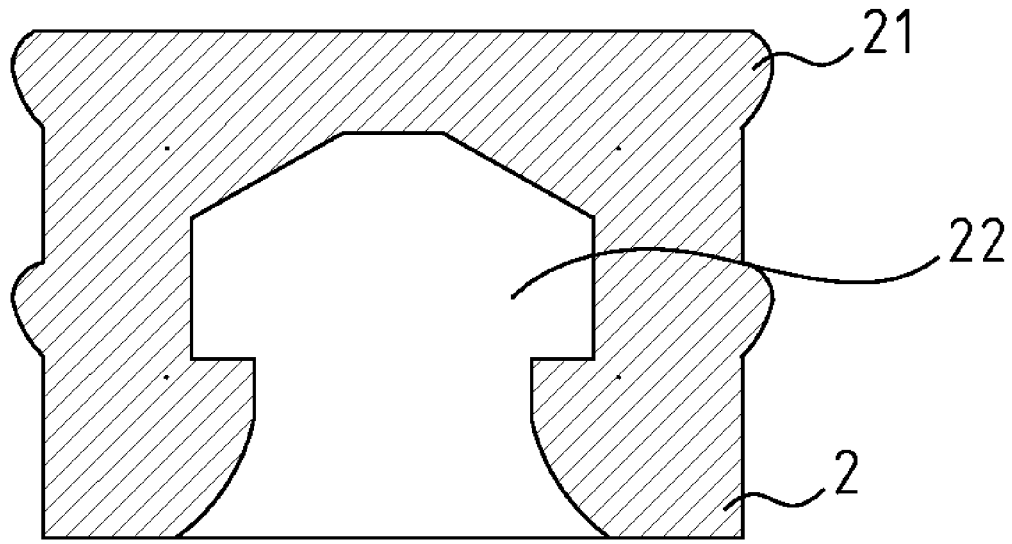
FIG. 3 is a cross sectional view of a rubber stopper of the disposable blood sampling device according to the present invention.

As shown in FIG. 3, the rubber stopper 2 is preferably made of a resilient material. At least a ring-shaped rib 21 is formed on a circumferential surface of the rubber stopper 2 and a fastening slot 22 is formed in the rubber stopper 2 for engaging with the fastening element 11, such that the rubber stopper 2 can be fixed to the second end of the plunger 1.

Figure 4:
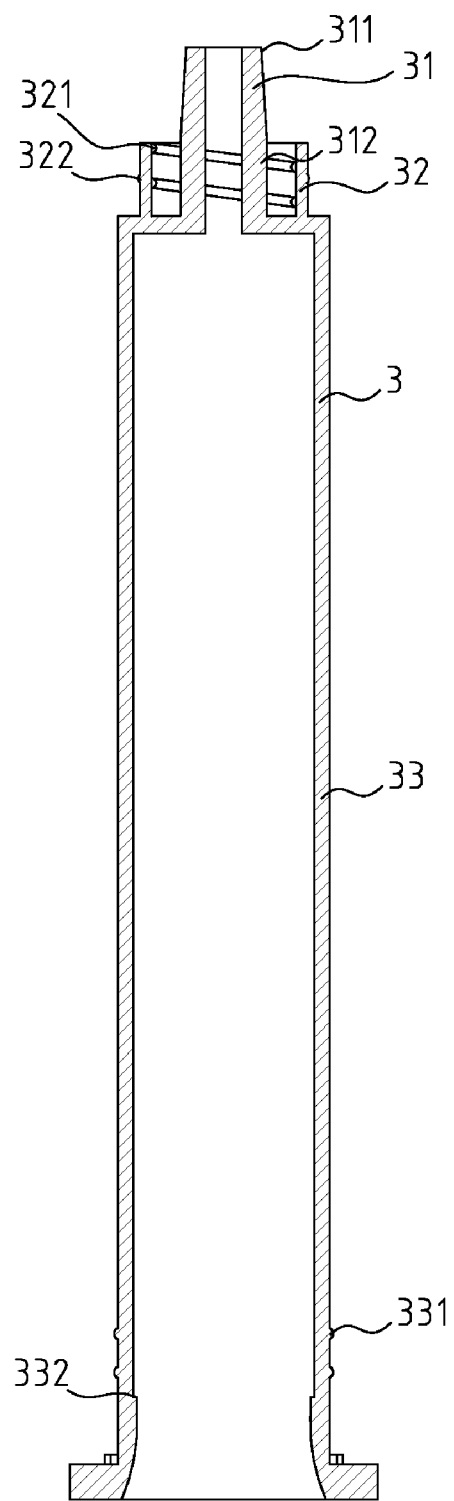
FIG. 4 is a cross sectional view of a barrel of the disposable blood sampling device according to the present invention.

As shown in FIG. 4, a barrel 3 has an axially extended tube body 33 with a first end and a second end opposite to the first end. A chamber is defined in the tube body 33 from the first end to the second end and has a width closely fitted for the rubber stopper 2. The second end of the tube body 33 has a needle connector 31 communicated to the chamber, and a ring-shaped flange 32 formed around the needle connector 31 and having an inner spiral protrusion 321 formed on an inner surface thereof. A free end of the needle connector 31 has a tapered portion 311 extending axially and outwardly a predetermined length. The ring-shaped flange 32 of the barrel 3 has a first ring-shaped protrusion 322 formed on an outer circumferential surface thereof and the tube body 33 of the barrel 3 has an inner protrusion 332 formed on the inner circumferential surface thereof close to the first end thereof. The tube body 33 of the barrel 3 has a second ring-shaped protrusion 331 formed on an outer circumferential surface thereof close to the first end.

Figure 5:
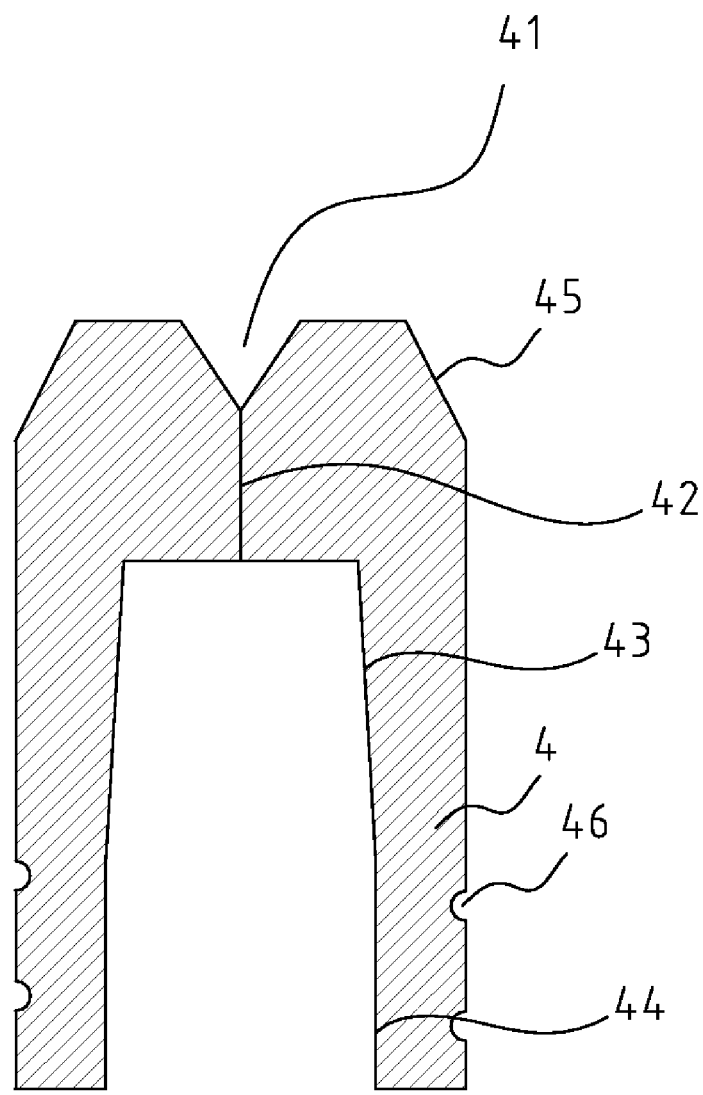
FIG. 5 is a cross sectional view of a sealing member of the disposable blood sampling device according to the present invention.

As shown in FIG. 5, a sealing member 4, which is made of resilient material, has a first end and a second end opposite to the first end, wherein an outer spiral groove 46 is formed on an outer circumferential surface of the sealing member 4 for engaging with the inner spiral protrusion 321 of the barrel 3, a blind hole is formed from the first end to the second end of the sealing member 4 for receiving the needle connector 31, a conical hole 41 is formed on the second end, and a sealing hole 42 is provided to connect the blind hole and conical hole 41 and is sealed when there is no external force applied thereto. The blind hole can be replaced with a cylindrical hole 44 and a tapered cylindrical hole 43 in sequence formed from first end to the second end for matching with an outer contour of the needle connector 31. The sealing member 4 has a tapered portion 45 defined at the second end thereof.

Figure 6:
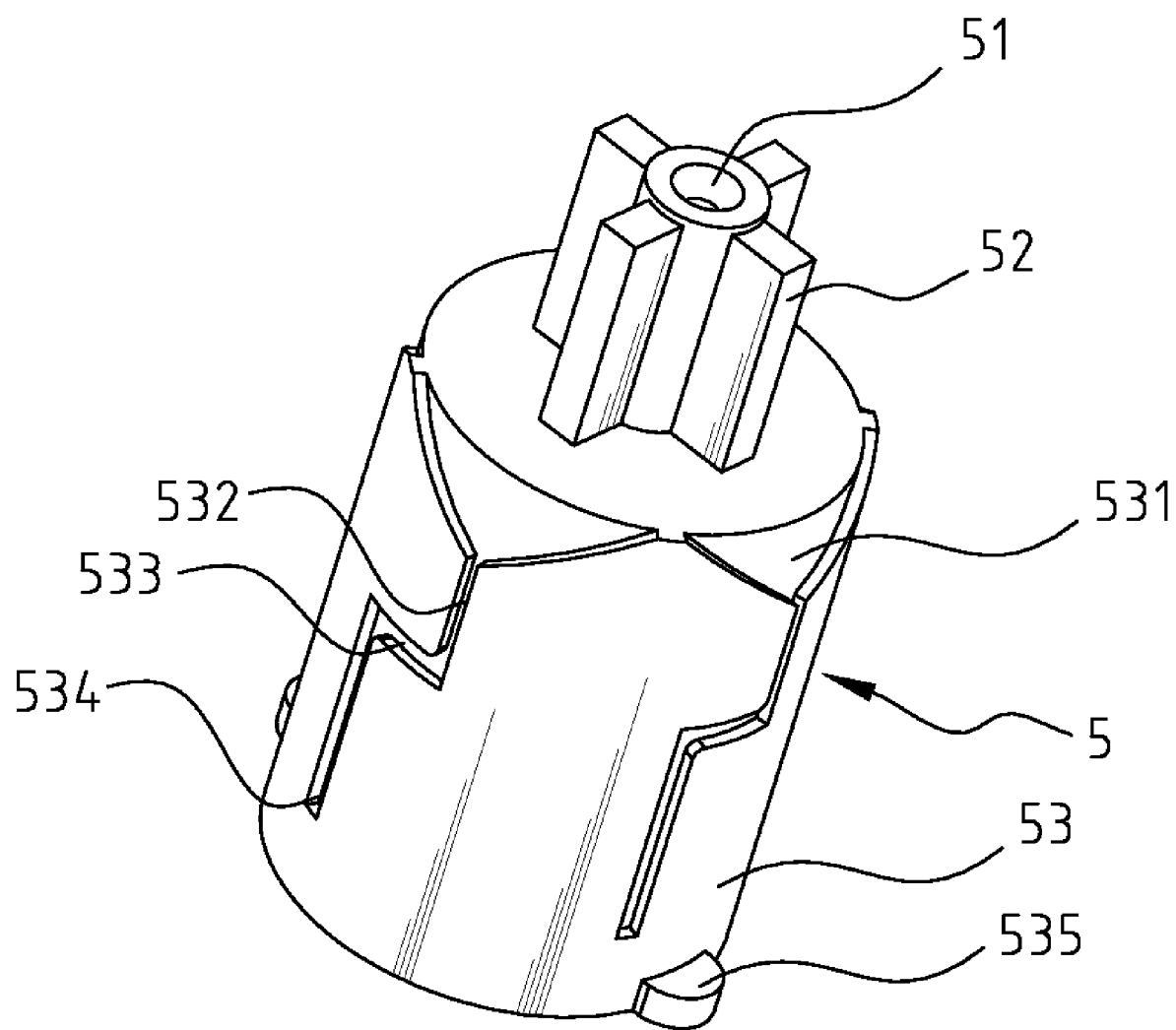
FIG. 6 is a perspective view of a needle holder of the disposable blood sampling device according to the present invention.
Figure 6A:
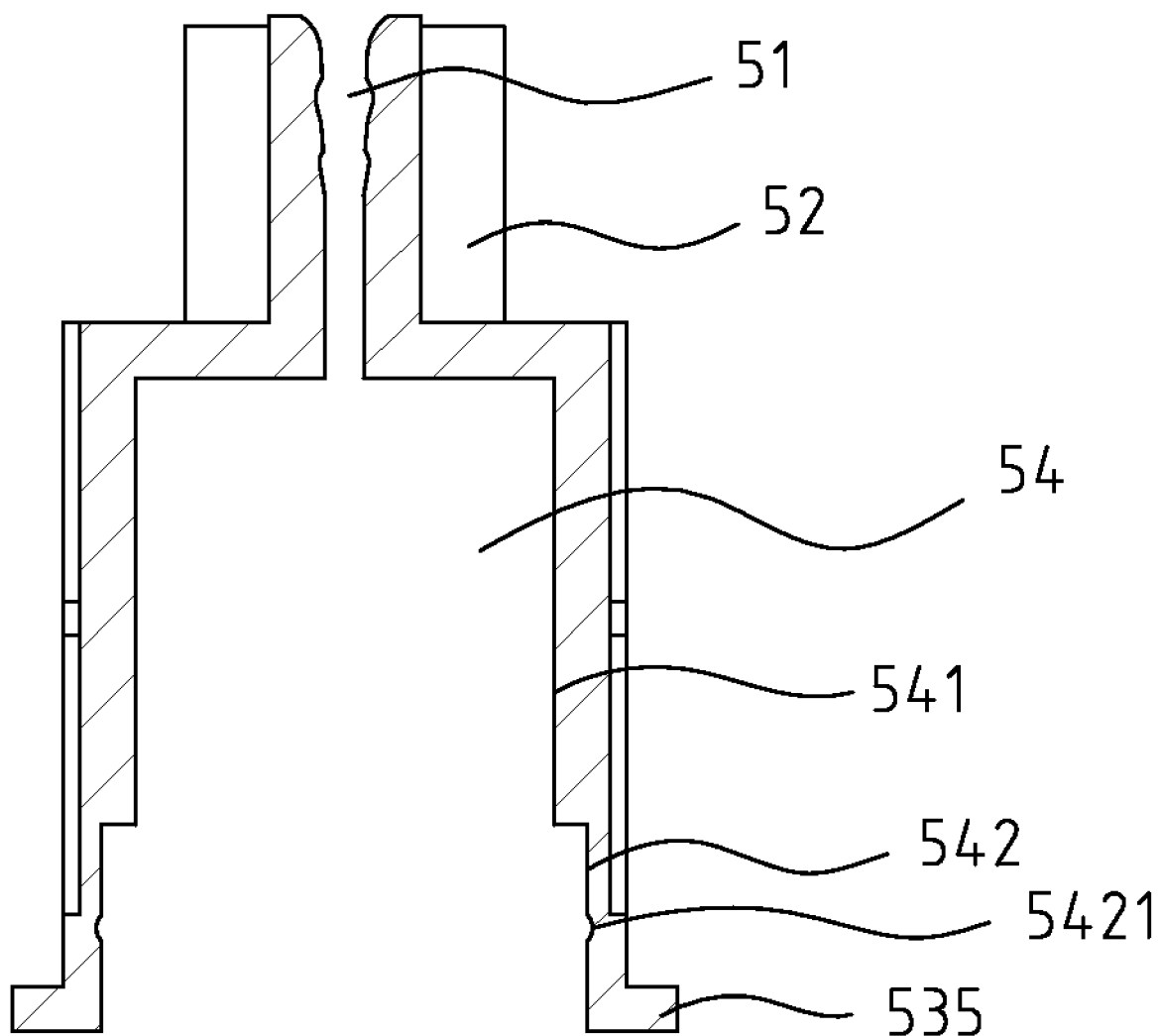
FIG. 6A is a cross sectional view of FIG. 6.

Referring to FIGS. 6 and 6A, the needle holder 5 in accordance with a preferred embodiment of the present invention has a first end and a second end opposite to the first end. A chamber 54 is formed in the needle holder 5 from the first end to the second end. The second end of the needle holder 5 has a needle-holding hole 51 communicated to the chamber 54 and a plurality of fins 52 provided around the needle-holding hole 51 for reinforcing the strength of the needle-holding hole 51. An outer circumferential surface of the needle holder 5 has a plurality of guide notches 531, first longitudinal guide grooves 532 connected to the guide notches 531, transversal guide grooves 533 connected to the first longitudinal guide grooves 532, second longitudinal guide grooves 534 connected to the transversal guide grooves 533. The guide notches 531 and the first longitudinal guide grooves 532 are jointly formed in Y-shape, and the first longitudinal guide grooves 532, the transversal guide grooves 533 and the second longitudinal guide grooves 534 are jointly formed in Z-shape. Two outer protrusions 535 are respectively formed on the outer circumferential surface of the needle holder 5 close to the first end. The chamber 54 of the needle holder 5 has a first inner wall 542 close to first end of the needle holder 5 and a second inner wall 541 close to the second end of the needle holder 5, wherein the first inner wall 542 has an inner diameter greater than the inner diameter of the second inner wall 541, and a ring-shaped groove 5421 is formed on the first inner wall 542 for engaging with the first ring-shaped protrusion 322 of the barrel 3.

The needle 6 is inserted into the needle-holding hole 51 of the needle holder 5 and sealing hole 42 of the sealing member 4.

Figure 7:
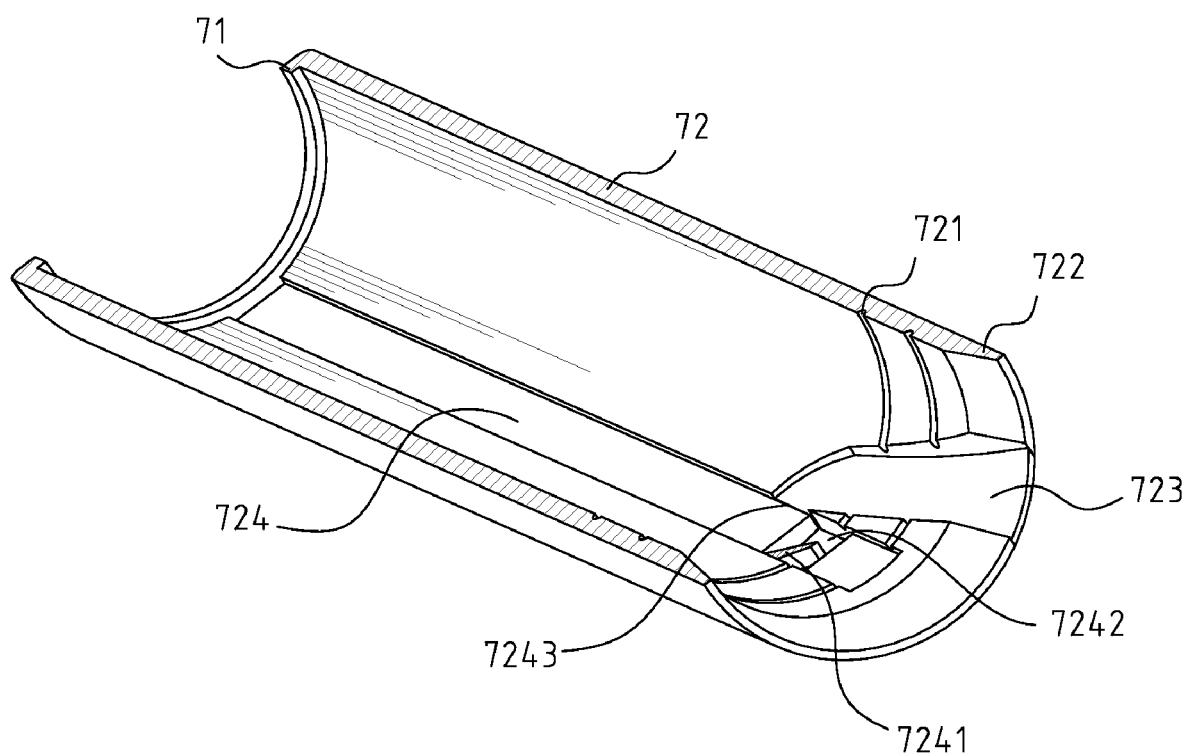
FIG. 7 is a perspective view of a portion of a protection sleeve of the disposable blood sampling device according to the present invention.
Figure 7A:
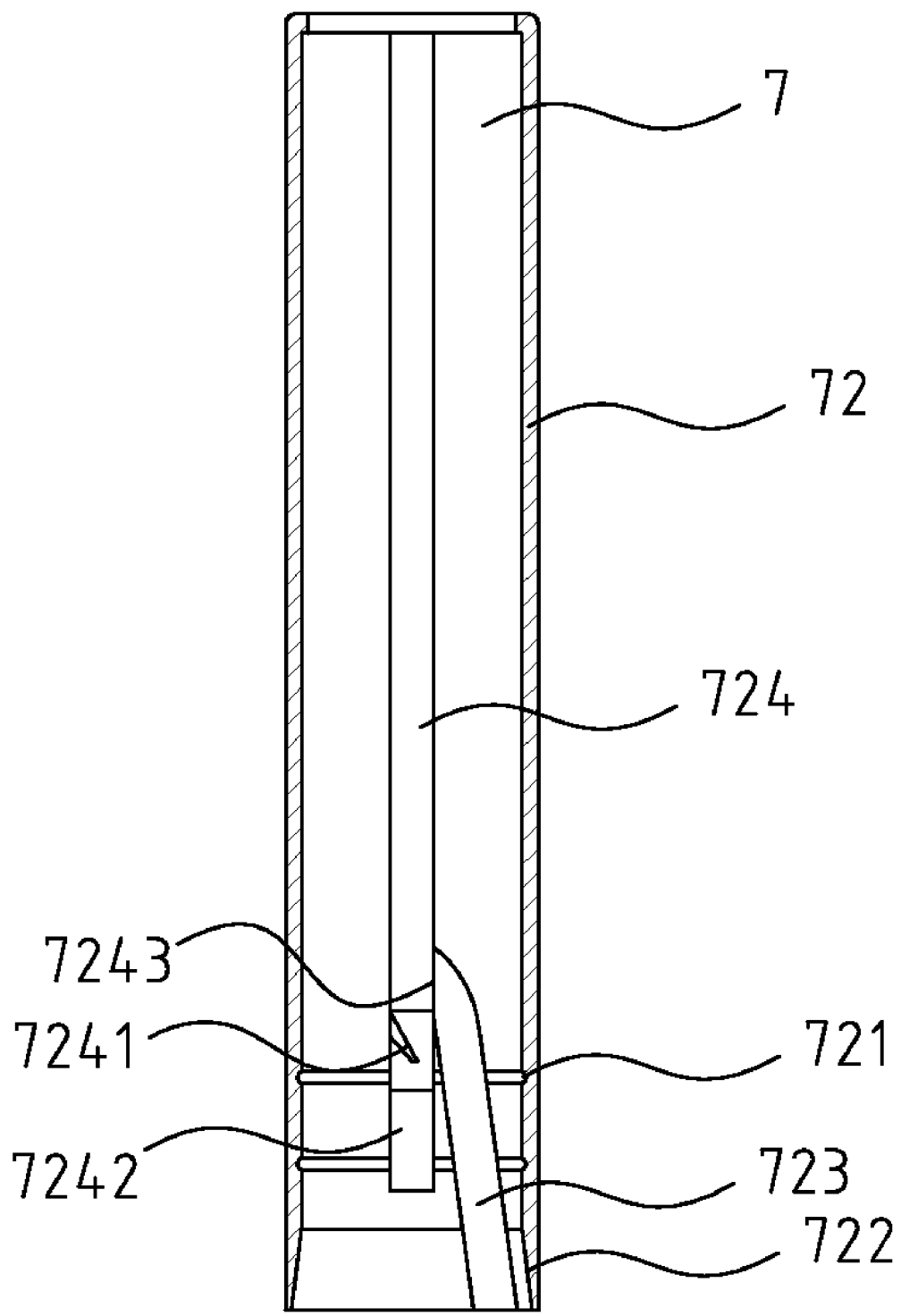
FIG. 7A is a cross sectional view of a protection sleeve according to the present invention.

Referring to FIGS. 7 and 7A, a protection sleeve 7 having an axially extended tube body with a first end and a second end opposite to the first end, wherein a passage is confined by an inner wall of the tube body and is formed from the first end to the second end. The inner wall has a guide slot 723 formed from the first end toward the second end, a longitudinal slot 724 communicated to the guide slot 723 for guiding the outer protrusion 535 of needle holder 5 and a step 7243 defined between the longitudinal slot 724 and guide slot 723. An end of the longitudinal slot 723 close to the first end of the protection sleeve 7 has a through hole 7242 with an elastic member 7241 protruded to a center of the through hole 724. An inner circumferential surface of the protection sleeve 7 close to the second end has an inner protrusion 71 with an inner diameter smaller than an outer diameter of the outer protrusion 535 of the needle holder 5. The inner wall of the protection sleeve 7 further has a ring-shaped groove 721 for engaging with the second ring-shaped protrusion 331 of the barrel 3. The passage of the protection sleeve 7 has an inclined guide surface 722 close to the first end of the protection sleeve 7.

Figure 8:
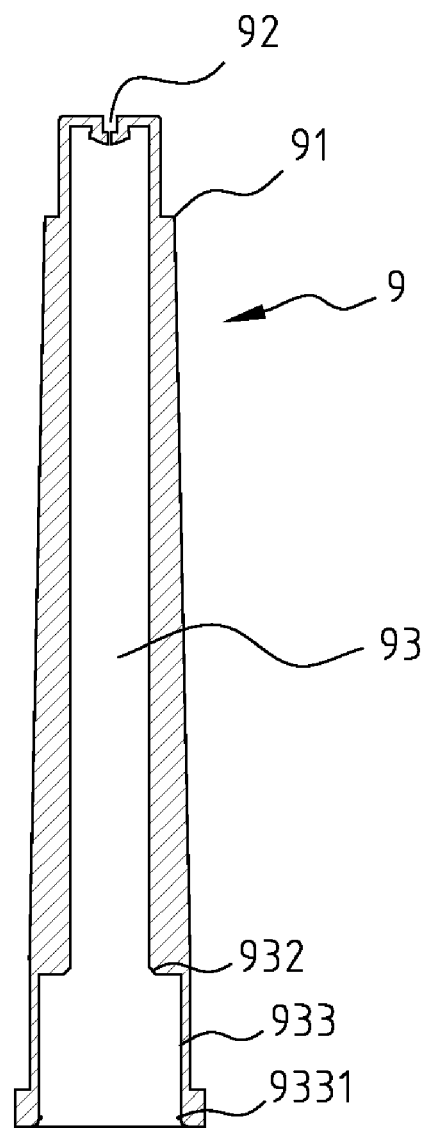
FIG. 8 is a cross sectional view of a needle sheath of the disposable blood sampling device according to the present invention.

Referring to FIG. 8, a needle sheath 9 has an axially extended tube body with a first end and a second end opposite to the first end, wherein a chamber 93 is formed in the needle sheath 9 from the first end to the second end, and the first end has a lock slot 933 fitted with an outer diameter of the needle holder 5. The lock slot 933 has a plurality of lock pieces 9331 that can be movably engaged with the first longitudinal guide grooves 532, the transversal guide grooves 533 and the second longitudinal guide grooves 534. A lead angle 932 is formed between the lock slot 933 and the chamber 93 of the needle sheath 9. An air hole 92 is formed at the second end of the needle sheath 9 and is communicated to the chamber 93 of the needle sheath 9. An outer surface of the needle sheath 9 has a plurality of ridges 91 axially formed for reinforcing the structural strength of the needle sheath 9.

The anticoagulant storing tube 8 is used to store an anticoagulant and is disposed in the chamber 93 close to the second end of the needle sheath 9.

In the following, the description will be made with reference to FIG. 9-16 and dedicated how the disposable blood sampling device is assembled.

Figure 9:
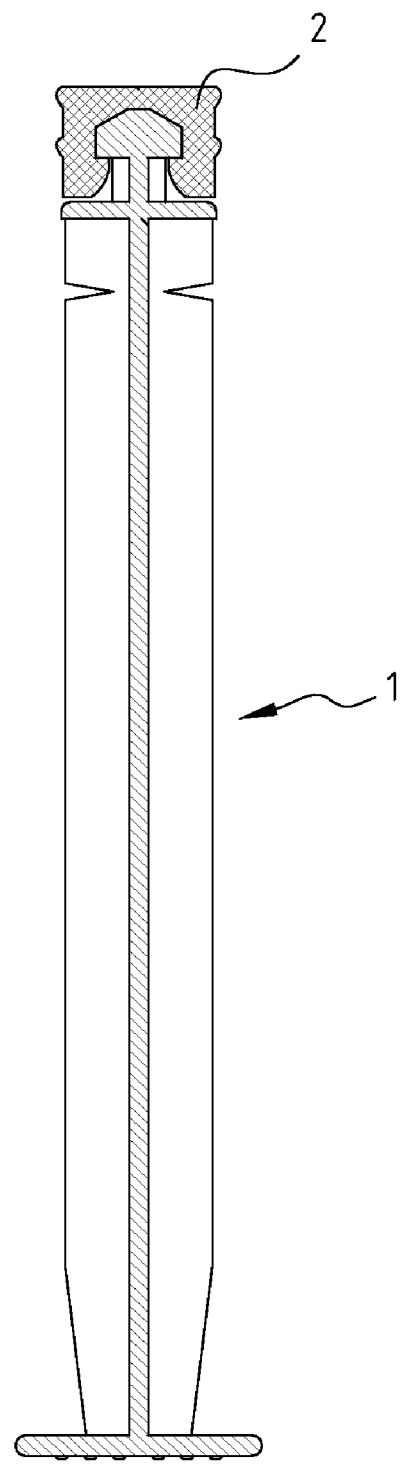
FIG. 9 is a cross sectional view of a combination of the plunger and the rubber stopper of the disposable blood sampling device according to the present invention.
Figure 10:
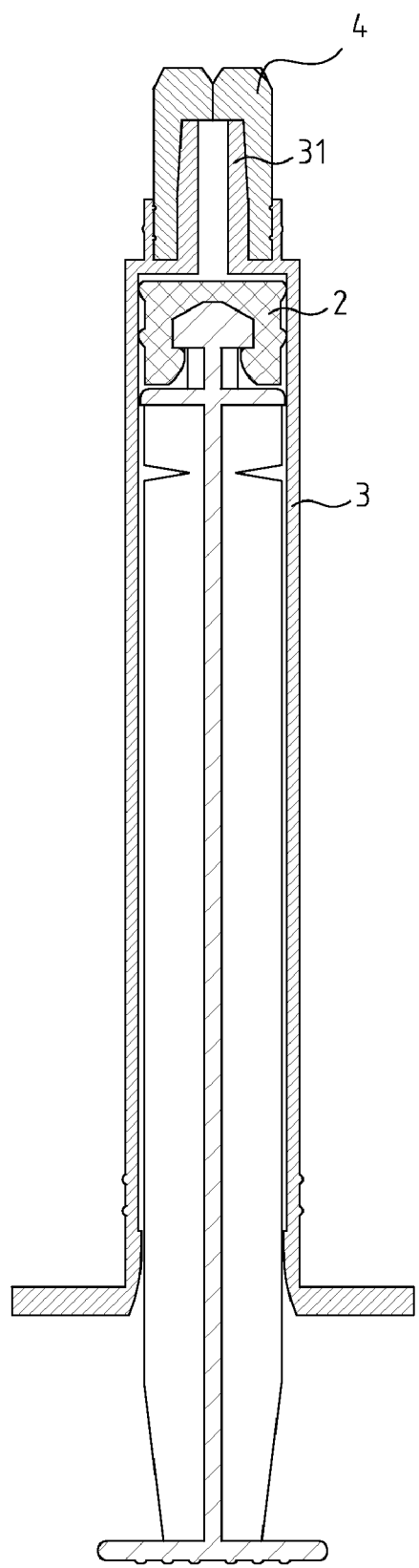
FIG. 10 is a cross sectional view of a combination of the plunger, rubber stopper, needle, barrel and sealing member of the disposable blood sampling device according to the present invention.
Figure 11:
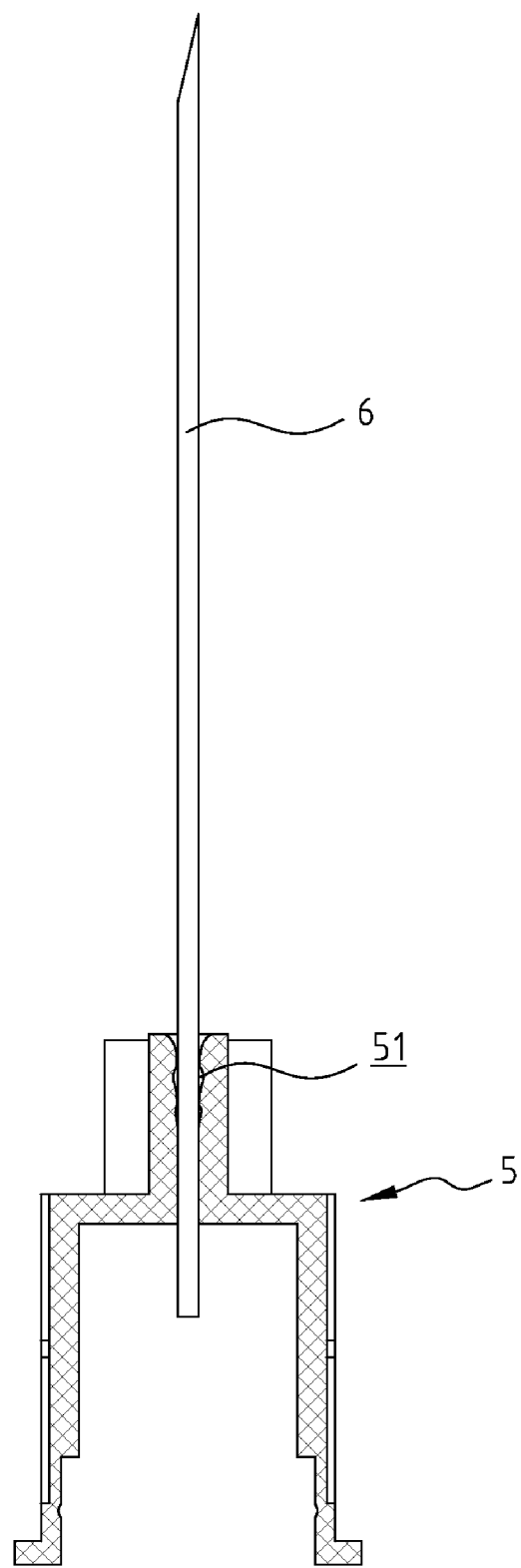
FIG. 11 is a cross sectional view of a combination of the needle and the needle holder of the disposable blood sampling device according to the present invention.
Figure 12:
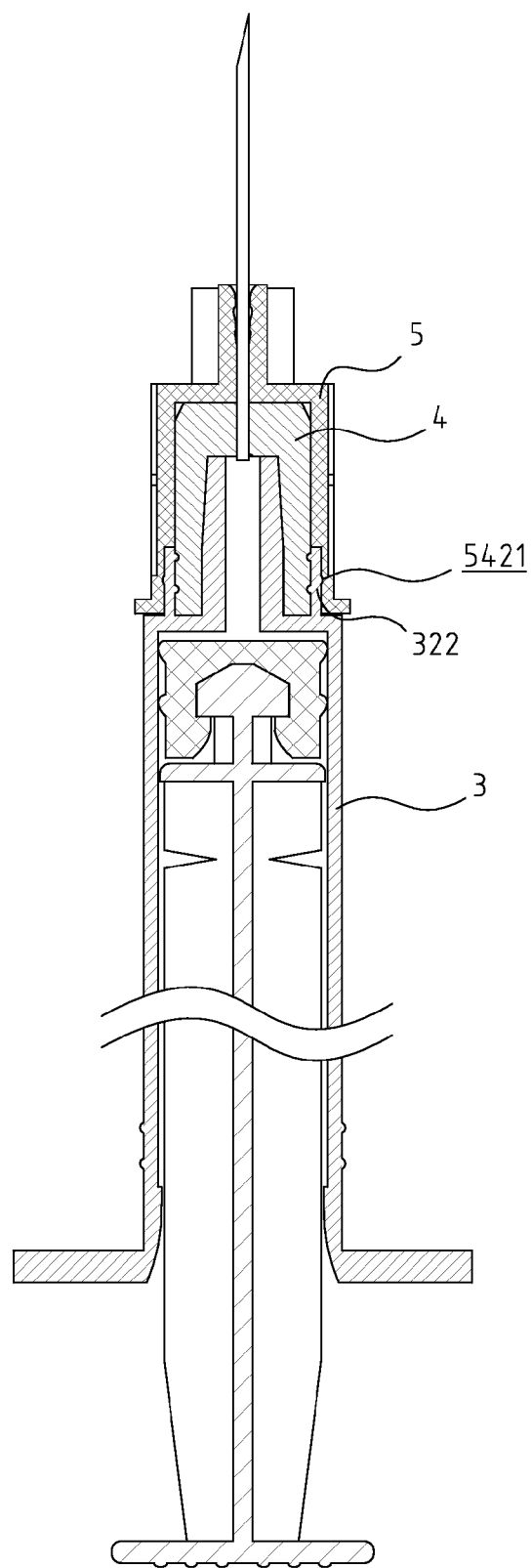
FIG. 12 is a cross sectional view of a combination of the plunger, rubber stopper, barrel, sealing member, needle holder and needle of the disposable blood sampling device according to the present invention.
Figure 13:
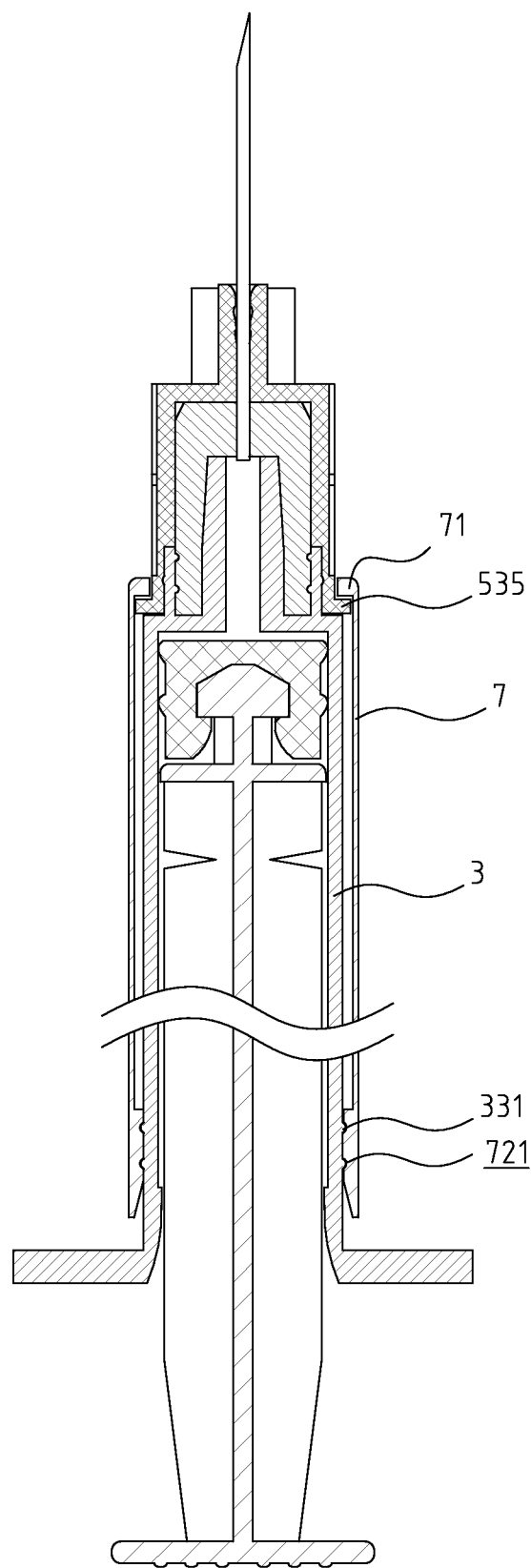
FIG. 13 is a cross sectional view of a combination of the plunger, rubber stopper, barrel, sealing member, needle holder, needle and needle sheath of the disposable blood sampling device according to the present invention.
Figure 14:
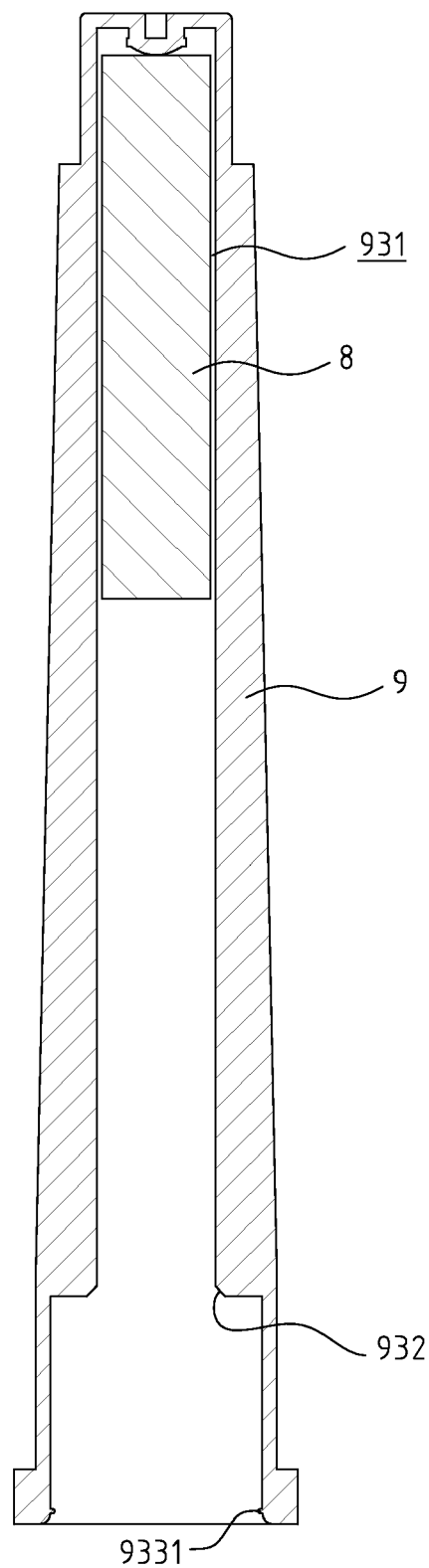
FIG. 14 is a cross sectional view of a combination of the needle sheath and the anticoagulant storing tube of the disposable blood sampling device according to the present invention.
Figure 15:
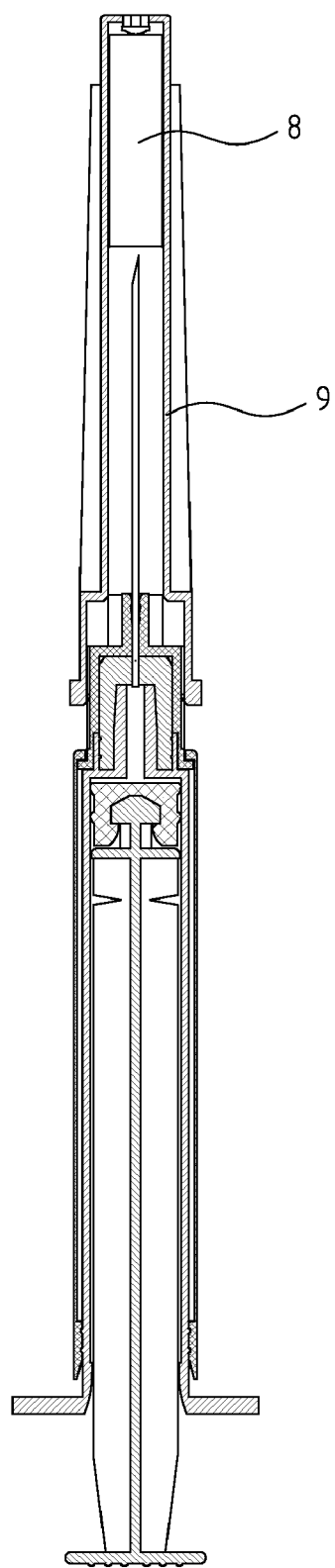
FIG. 15 is a cross sectional view of an assembled disposable blood sampling device according to the present invention.
Figure 16:
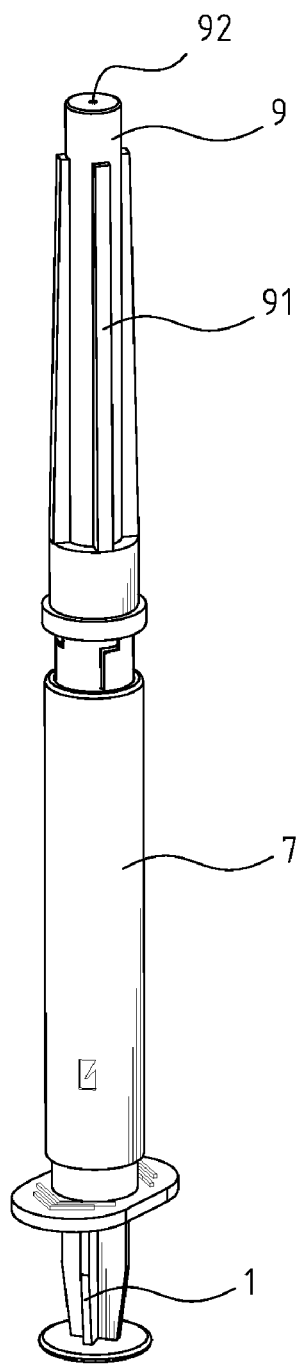
FIG. 16 is a perspective view of an assembled disposable blood sampling device according to the present invention.

At first, the rubber stopper 2 is coupled to the second end of the plunger 1 (see FIG. 9). Then, the plunger with the rubber stopper is pushed into the chamber of the barrel 3, and then the sealing member 4 is rotatably sleeved on the needle connector 31 of the barrel 3, such that the outer spiral groove 46 of the sealing member 4 is engaged with the inner spiral protrusion 321 of the barrel 3. Subsequently, the needle 6 is inserted into the needle-holding hole 51 of the needle holder 5 (see FIG. 11). The needle holder 5 is sleeved and fixed onto the sealing member 4 by engaging the ring-shaped groove 5421 of the needle holder 5 with the first ring-shaped protrusion 322 of the barrel 3 (see FIG. 12). Next, the protection sleeve 7 is sleeved onto the tube body 33 of barrel 3 from first end thereof until the outer protrusion 535 of the needle holder 5 blocks the inner protrusion 71 of the protection sleeve 7, and at the same time, the ring-shaped groove 721 is engaged with the second ring-shaped protrusion 331 of the barrel 3 (see FIG. 13). After the anticoagulant storing tube 8 is disposed in the chamber 93 of the needle sheath 9 close to the second end as shown in FIG. 14, the needle sheath 9 is sleeved onto the needle holder 5 by inserting the locking piece 9331 of the needle sheath 9 into the transversal guide grooves 533 from the guide notches 531 of the needle holder 5 (see FIG. 15 and FIG. 16).

In the following, the description will be made with reference to FIG. 17-23 and dedicated how the disposable blood sampling device is used.

Figure 17:
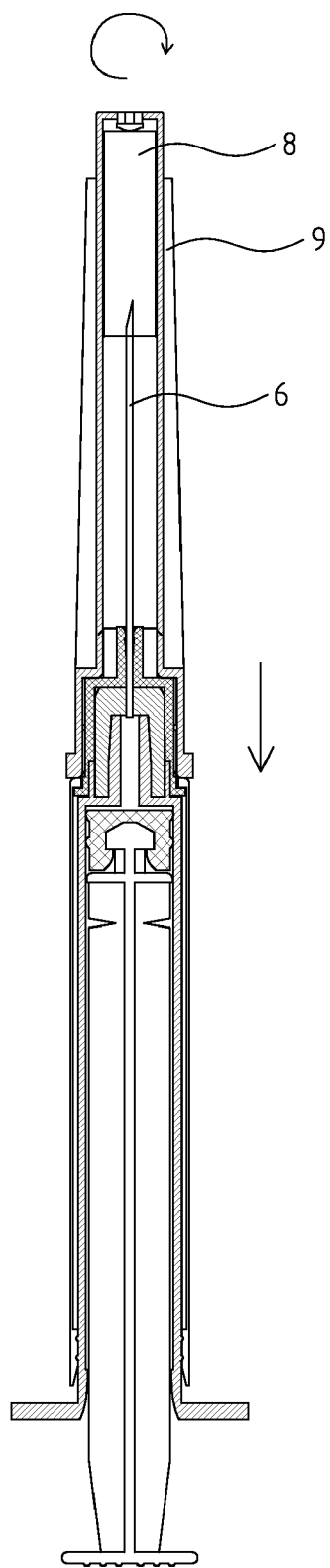
FIG. 17 is a schematic view showing that the needle is inserted into the anticoagulant storing tube according to the present invention.
Figure 18:
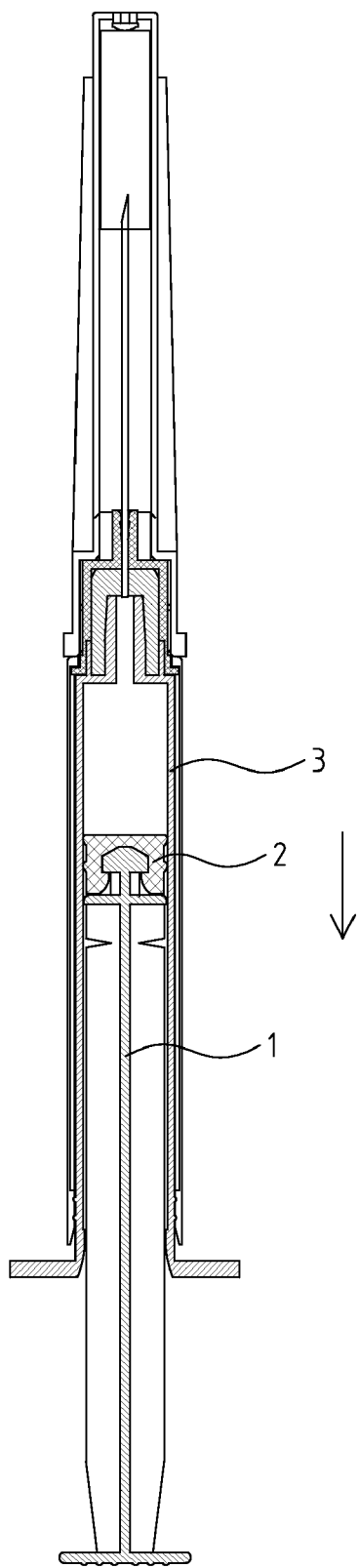
FIG. 18 is a schematic view showing that the plunger is moved axially to exhaust the anticoagulant according to the present invention.
Figure 19:
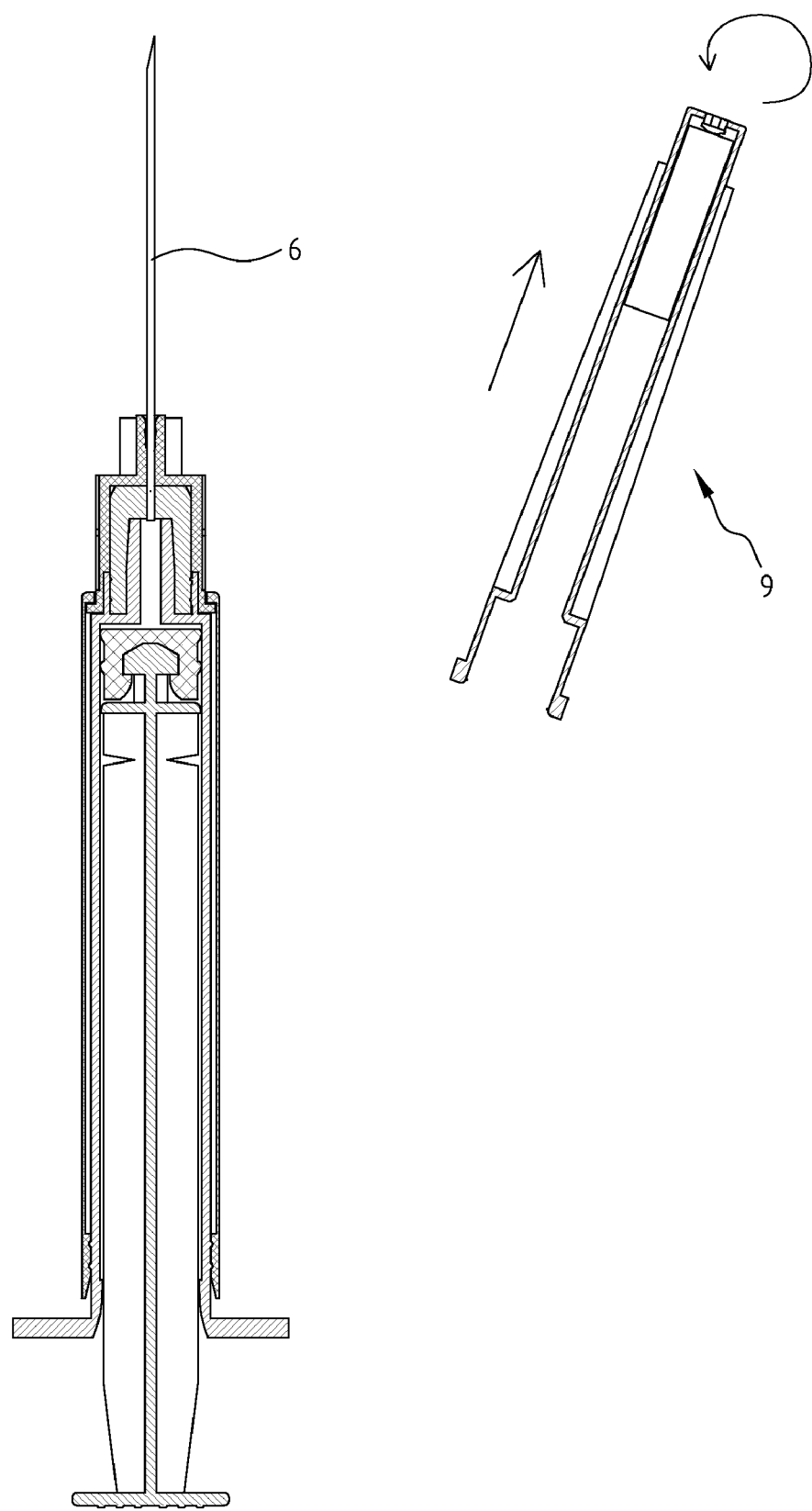
FIG. 19 is a schematic view showing that the protection sleeve is removed from the barrel ready for use according to the present invention.
Figure 20:
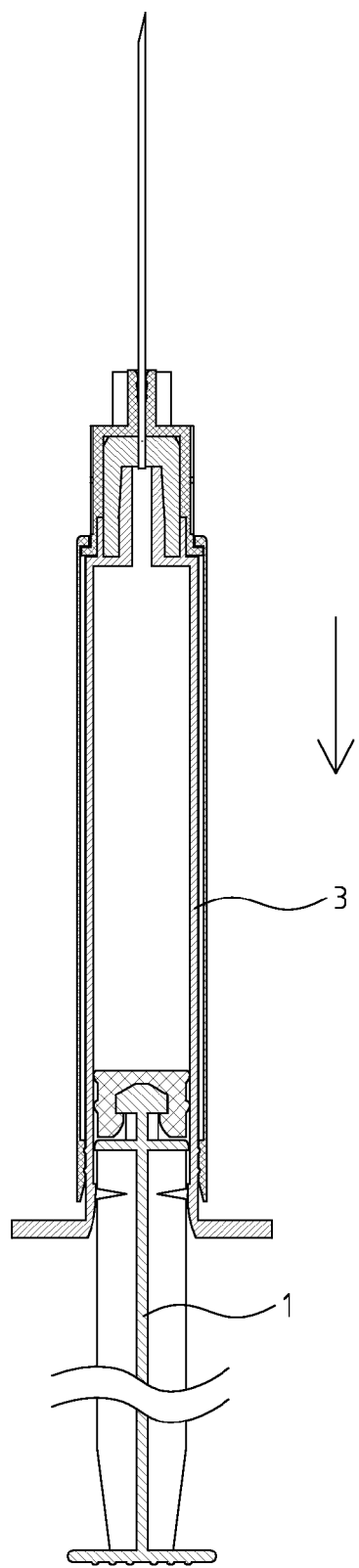
FIG. 20 is a schematic view showing that barrel of the disposable blood sampling device is filled with blood according to the present invention.
Figure 21:
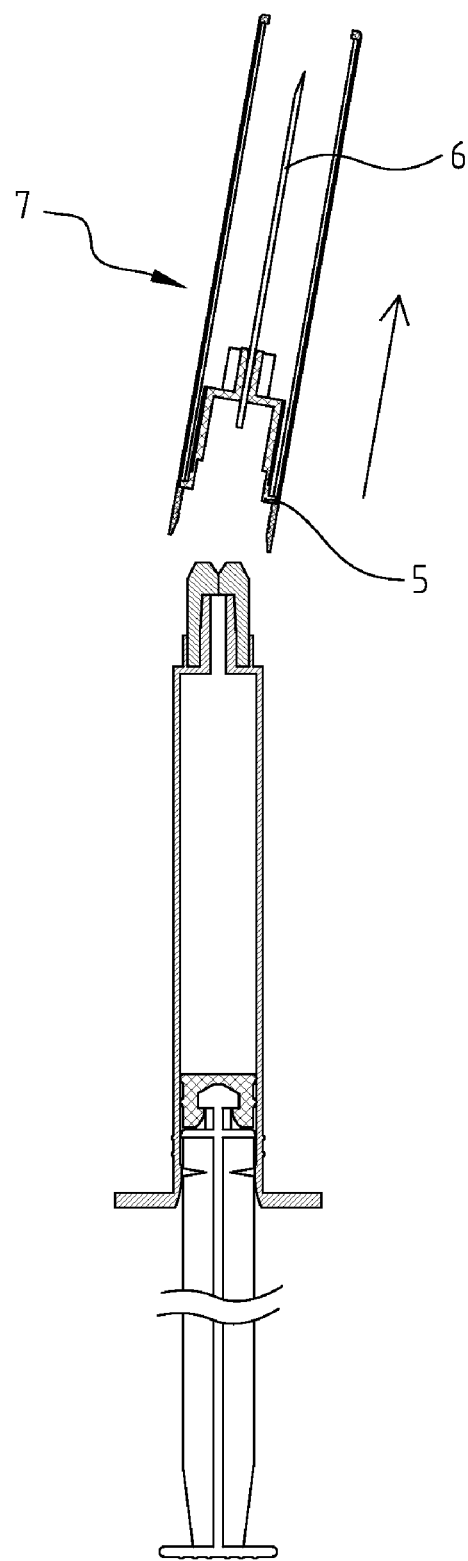
FIG. 21 is a schematic view showing that the needle is hidden in the protection sleeve and removed from the sealing member.
Figure 22:
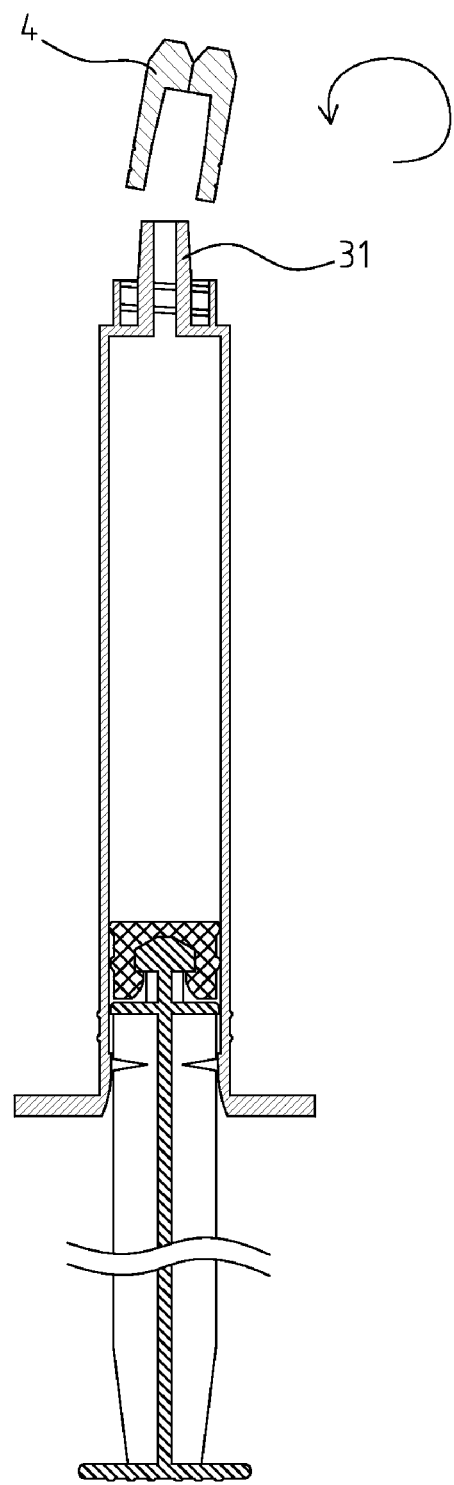
FIG. 22 is a schematic view showing that the sealing member is removed from the barrel.
Figure 23:
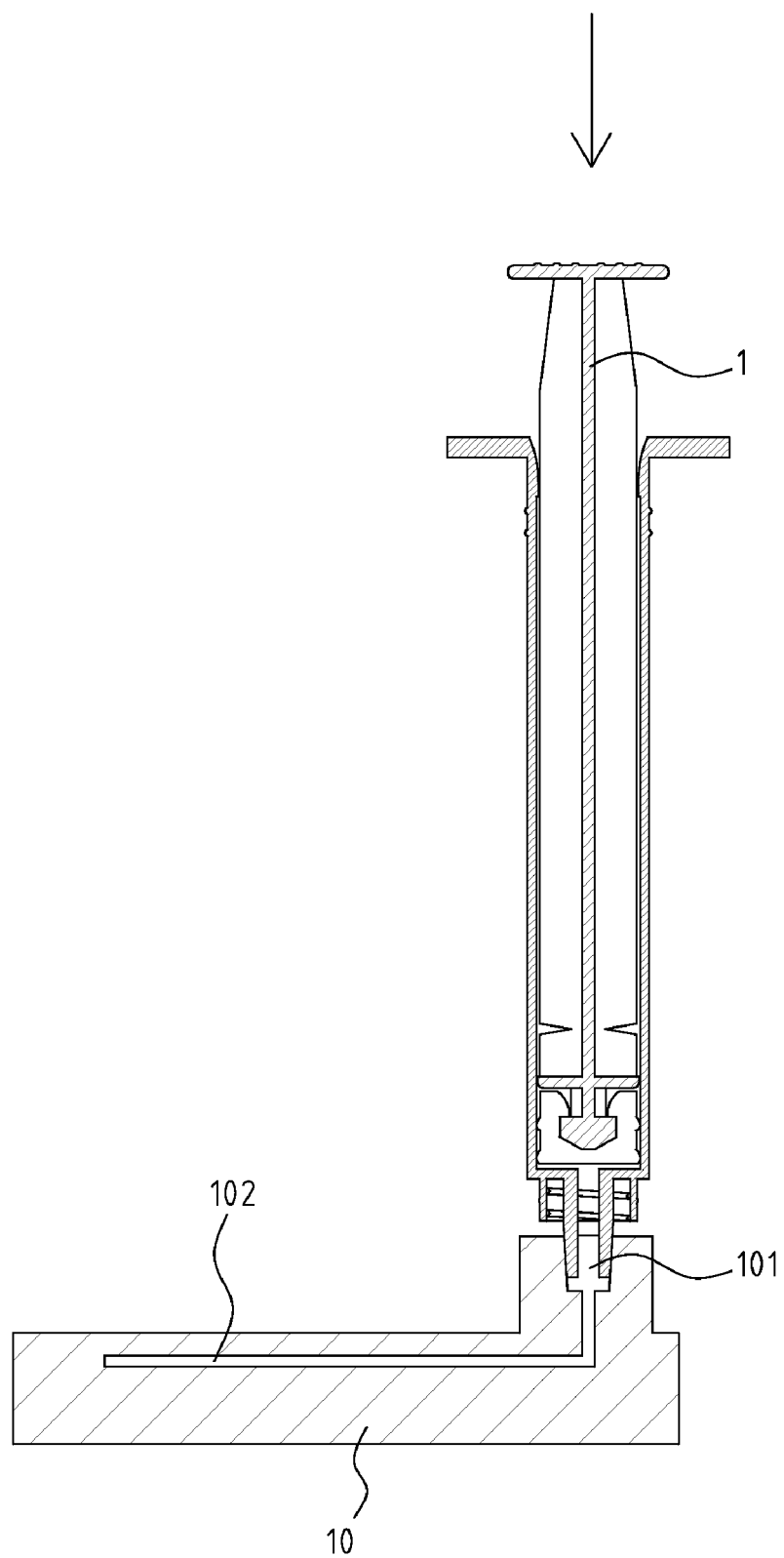
FIG. 23 is a schematic view showing that the blood in the disposable blood sampling device is inserted into a blood culture dish according to the present invention.

At first, the needle sheath 9 is rotated to make the lock piece 9331 move along the transversal guide grooves 533 to the second longitudinal guide groove 534 of the needle holder 5, such that the needle sheath 9 can be pressed downwardly to let the needle 6 insert into the anticoagulant storing tube 8 as shown in FIG. 17. Then, pull the plunger 1 with the rubber stopper 2 backwardly within the barrel 3 so that the anticoagulant can be drawn into the chamber of the barrel 3 (see FIG. 18). Subsequently, push the plunger 1 forwardly to exhaust the anticoagulant out of the barrel 3. At this time, draw the needle sheath 9 forward to let the lock piece 9331 move from the second longitudinal guide grooves 534 to the transversal guide groove 533 and then, rotate the needle sheath 9 to let the lock piece 9331 move to the first longitudinal guide grooves 532, and finally draw the needle sheath 9 forward again to remove the lock piece 9331 from the needle holder 5 along the first longitudinal guide grooves 532 and guide notches 531, such that the needle sheath 9 can be detached from the needle holder 5 (see FIG. 19). To obtain a sample of blood from a human body, the needle 6 is first inserted into a blood vessel of the human body, and then the plunger 1 is pulled for drawing the blood into the chamber of the barrel 3, as shown in FIG. 20. After the sample of blood is obtained, the needle 6 can be detached from the blood sampling device by drawing the protection sleeve 7 forwardly until the needle 6 is entirely hidden in the protection sleeve 7, such that the ring-shaped grooves 721 of the protection sleeve 7 is disengaged with the second ring-shaped protrusion 331 of the barrel 3. At this time, the outer protrusion 535 of the needle holder 5 is pressed against an end of the longitudinal guide slot 724 of the protection sleeve 7. Then, a force may be applied to separate the protection sleeve 7 with the needle 6 from the needle holder 6, as shown in FIG. 21. To obtain the sample of the blood in the barrel 3, the sealing member 4 has to be removed from the barrel 3 first, as shown in FIG. 22. Next, the needle connector 31 is inserted into an instill hole 101 of a blood culture dish 10 as shown in FIG. 23. Then, the plunger 1 is pushed to press the blood in the chamber of the barrel 3 into a blood storing trough 102 of the blood culture dish 10 through the instill hole 101.

Although the present invention has been described with reference to the preferred embodiment thereof, it is apparent to those skilled in the art that a variety of modifications and changes may be made without departing from the scope of the present invention which is intended to be defined by the appended claims.

What is claimed is:

1. A disposable blood sampling device, comprising:
   a plunger having a first end and a second end opposite to the first end;
   a rubber stopper coupled to the second end of the plunger;
   a barrel having an axially extended tube body with a first end and a second end opposite to the first end, wherein a chamber is defined in the tube body from the first end to the second end and has a width closely fitted for the rubber stopper, and the second end has a needle connector communicated to the chamber, and a ring-shaped flange formed around the needle connector and having an inner spiral protrusion formed on an inner surface thereof;
   a sealing member, which is made of resilient material, having a first end and a second end opposite to the first end, wherein an outer spiral groove is formed on an outer circumferential surface of the sealing member for engaging with the inner spiral protrusion of the barrel, a blind hole is formed from the first end to the second end for receiving the needle connector, a conical hole is formed on the second end, and a sealing hole is provided to connect the blind hole and conical hole and is sealed when there is no external force applied thereto;
   a needle holder having a first end and a second end opposite to the first end, wherein a chamber is formed in the needle holder from the first end to the second end, the second end has a needle-holding hole communicated to the chamber, an outer circumferential surface of the needle holder has a plurality of guide notches, first longitudinal guide grooves connected to the guide notches, transversal guide grooves connected to the first longitudinal guide grooves, second longitudinal guide grooves connected to the transversal guide grooves, and an outer protrusion;

a needle inserted into the needle-holding hole of the needle holder and the sealing hole of the sealing member;

a protection sleeve having an axially extended tube body with a first end and a second end opposite to the first end, wherein a passage is confined by an inner wall of the tube body and is formed from the first end to the second end, the inner wall has a guide slot formed from the first end toward the second end, a longitudinal slot communicated to the guide slot for guiding the outer protrusion of needle holder and a step defined between the longitudinal slot and guide slot, an end of the longitudinal slot close to the first end of the protection sleeve has a through hole with an elastic member protruded to a center of the through hole, an inner circumferential surface of the protection sleeve close to the second end has an inner protrusion with an inner diameter smaller than an outer diameter of the outer protrusion of the needle holder;

a needle sheath having an axially extended tube body with a first end and a second end opposite to the first end, wherein a chamber is formed in the needle sheath from the first end to the second end, and the first end has a lock slot fitted with an outer diameter of the needle holder; and an anticoagulant storing tube disposed in the chamber of the needle sheath and close to the second end of the needle sheath.

2. The disposable blood sampling device as claimed in claim 1, wherein the plunger has a plurality of notches extending from an outer perimeter to an axis thereof close to the second end, such that the plunger can be broken off for convenient disposal by applying a force to the notches.

3. The disposable blood sampling device as claimed in claim 1, wherein a free end of the needle connector has a tapered portion extending axially and outwardly a predetermined length.

4. The disposable blood sampling device as claimed in claim 3, wherein the ring-shaped flange of the barrel has a first ring-shaped protrusion formed on an outer circumferential surface thereof and the tube body of the barrel has an inner protrusion formed on the inner circumferential surface thereof close to the first end.

5. The disposable blood sampling device as claimed in claim 3, wherein the tube body of the barrel has a second ring-shaped protrusion formed on an outer circumferential surface thereof close to the first end, and the inner wall of the protection sleeve has a ring-shaped groove for engaging with the second ring-shaped protrusion.

6. The disposable blood sampling device as claimed in claim 1, wherein the sealing member has a tapered portion defined at the second end thereof.

7. The disposable blood sampling device as claimed in claim 6, wherein the sealing member has a cylindrical hole and a tapered cylindrical hole in sequence formed from first end to the second end thereof.

8. The disposable blood sampling device as claimed in claim 1, wherein the guide notches and the first longitudinal guide grooves of the needle holder are jointly formed in Y-shape, and the first longitudinal guide grooves, the transversal guide grooves and the second longitudinal guide grooves of the needle holder are jointly formed in Z-shape.

9. The disposable blood sampling device as claimed in claim 7, wherein the second end of the needle holder has a plurality of fins provided around the needle-holding hole.

10. The disposable blood sampling device as claimed in claim 9, wherein the chamber of the needle holder has a first inner wall close to first end of the needle holder and a second inner wall close to the second end of the needle holder, wherein the first inner wall has an inner diameter greater than the inner diameter of the second inner wall, and a ring-shaped groove is formed on the first inner wall for engaging with the first ring-shaped protrusion of the barrel.

11. The disposable blood sampling device as claimed in claim 1, wherein the passage of the protection sleeve has an inclined guide surface close to the first end of the protection sleeve.

12. The disposable blood sampling device as claimed in claim 1, wherein the needle sheath has an air hole formed at the second end thereof and the air hole is communicated to the chamber of the needle sheath.

13. The disposable blood sampling device as claimed in claim 12, wherein a lead angle is formed between the lock slot and the chamber of the needle sheath.

* * * * *